United States Patent [19]

Denman et al.

[11] Patent Number: 5,756,687
[45] Date of Patent: May 26, 1998

[54] ISOLATION OF COMPONENTS OF INTEREST FROM MILK

[75] Inventors: Julie S. Denman, Medway; Edward S. Cole, Mendon, both of Mass.

[73] Assignee: Genzyme Transgenics Corporation, Framingham, Mass.

[21] Appl. No.: 376,620

[22] Filed: Jan. 23, 1995

Related U.S. Application Data

[63] Continuation of Ser. No. 28,395, Mar. 9, 1993, abandoned.

[51] Int. Cl.$^6$ .............. C07K 1/14; C07K 1/16; C07K 1/30; C07K 1/36
[52] U.S. Cl. .......... 530/412; 435/69.1; 435/70.1; 435/71.1; 435/183; 435/226; 530/413; 530/414; 530/350; 530/415; 530/416; 530/417; 530/418; 530/422; 530/832; 530/419
[58] Field of Search .............. 435/69.1, 70.1, 435/71.1, 183, 226; 530/412, 413, 414, 350, 415, 416, 417, 418, 422, 832, 419

[56] References Cited

U.S. PATENT DOCUMENTS

| | | | |
|---|---|---|---|
| 4,644,056 | 2/1987 | Kothe et al. | 530/387 |
| 4,898,826 | 2/1990 | Duffy et al. | 435/226 |
| 5,165,945 | 11/1992 | Yee et al. | 426/36 |
| 5,175,013 | 12/1992 | Huang et al. | 426/565 |
| 5,178,894 | 1/1993 | Rudel | 426/549 |

OTHER PUBLICATIONS

DiTullio, P. et al. (Jan. 1992) "Production of Cystic Fibrosis Transmembrane Conductance Regulator In The Milk of Transgenic Mice" *Bio/Technology*, 10:74–77.

Price, N.C., Enzyme Assays—A Practical Approach, "Techniques for Enzyme Extractions" (Oxford University Press 1992) 262–263.

Denman J. et al. (Sep. 1991) "Transgenic Expression Of A Variant Of Human Tissue–Type Plasminogen Activator In Goat Milk: Purification And Characterization Of The Recombinant Enzyme" *Bio/Technology*, 9:839–843.

Ebert, K.M. et al. (Sep. 1991) "Transgenic Production Of A Variant Of Human Tissue–Type Plasminogen Activator In Goat Milk: Generation Of Transgenic Goats And Analysis Of Expression" *Bio/Technology*, 9:835–838.

Heng, M.H. and Glatz, C.E. (1990) "Flux Enhancement in Hollow Fiber Ultrafiltration for the Recovery of Acid Cheese Whey Precipitates" *Biotechnol. Prog.*, 6:129–134.

Clark, A.J. et al. (May 1989) "Expression Of Human Anti–Hemophilic Factor IX In The Milk Of Transgenic Sheep" *Bio/Technology*, 7:487–492.

Gordon, K. et al. (Nov. 1987) "Production Of Human Tissue Plasminogen Activator In Transgenic Mouse Milk" *Bio/Technology*, 5:1183–1186.

Lau, D. et al. (Sep. 1987) "A Modified Human Tissue Plasminogen Activator With Extended Half–Life In Vivo" *Bio/Technology*, 5:953–958.

Groves, M.L. and Farrell, H.M. Jr. (1985) "Isolation and Characterization of New Proteins Produced by the Infusion of Colchicine in Goat Mammary Gland" *Biochim. et Biophys. Acta*, 844:105–112.

Davies, D.T. et al., Biochemistry of Lactation: The Composition of Milk, (ed. Mepham, T.B. Elsevier, NY 1983) 81.

Swaisgood, H.E., Developments in Dairy Chemistry—1. Industrial Isolation of Milk Proteins: Whey Proteins, "Chemistry of Milk Protein" (ed. Fox, P.F., Applied Science Publishers, NY 1982) 339–373.

Steimer, K.S. et al. (1981) "The Serum–Free Growth of Cultured Cells in Bovine Colostrum and in Milk Obtained Later in the Lactation Period" *J. Cell Physiol.*, 109(2):223–234.

Steimer, K.S. and Klagsbrun, M. (Feb. 1981) "Serum–Free Growth of Normal and Transformed Fibroblasts in Milk: Differential Requirements for Fibronectin" *J. Cell Biol.* 88(2):294–300.

Milk Proteins II—Chemistry and Molecular Biology, "Whole Casein: Isolation, Properties, and Zone Electrophoresis" (ed. McKenzie, H.A., Academic Press, Inc.) 88.

Okamoto et al., Thromb Haemost, 45(2), 121–6, 1981.

Goding, "Monoclonal Antibodies: Principles and Practices", Academic Press, 1986, pp. 109–110.

Christensen et al., Milchwissenschaft, 44:480–484, 1989 (Abstract thereof).

*Primary Examiner*—Ronald B. Schwadron
*Attorney, Agent, or Firm*—Lahive & Cockfield, LLP

[57] ABSTRACT

Methods of isolating components of interest from a milk sample are described. The methods include a step wherein the solubility of at least a portion of the total milk protein is stabilized in such a manner as to allow isolation of the component of interest without significant loss in yield. Kits for stabilizing the solubility of at least a portion of the total milk protein of the milk sample containing the component of interest also are described.

16 Claims, 8 Drawing Sheets

ISOLATION OF COMPONENTS OF INTEREST FROM MILK

This application is a continuation of application Ser. No. 08/028,395, filed on Mar. 9, 1993, now abandoned.

BACKGROUND OF THE INVENTION

Due to the long history of their inclusion in the human diet and the relative ease with which they can be isolated, naturally occurring milk components have been studied for many years. (Swaisgood, H. E., Developments in Dairy Chemistry-I: Chemistry of Milk Protein, (Applied Science Publishers, NY, 1982)). Recently, researchers have taken advantage of milk as a convenient source of proteins not normally produced in milk by directing the synthesis of particular proteins of interest to the mammary tissue of transgenic mammals. For example, researchers have incorporated a fusion gene composed of the regulatory sequence from the β-lactoglobulin gene and the coding sequence for the human anti-hemophilic factor IX gene into a sheep germline. (Clark, A. J. et al., (May 1989) Biotechnology 7:487–492). The lactating transgenic ewes subsequently secreted factor IX into their milk. Similarly, a goat germline has been engineered to include a fusion gene containing the regulatory sequences from the gene for murine whey acidic protein linked to the coding sequence for human longer-acting tissue-type plasminogen activator. (Ebert, K. M. et al., (September 1991) Biotechnology 9:835–838). Milk from the transgenic dairy goat contained the modified tissue plasminogen activator.

The production of proteins of interest, such as therapeutic agents, in the milk of transgenic livestock offers the possibility of large scale production of such proteins with an accompanying reduction of costs which are typically associated with the conventional production of complex recombinant proteins in mammalian cell culture systems. Although transgenic expression of proteins in milk presents advantages over more traditional methods of recombinant protein expression, it also poses several challenges. These include the preservation of the activity of the recombinant protein in milk and the purification of the protein to the required degree of purity for feasible commercial production.

Traditional methods of isolating a protein of interest from milk often included as one of their initial steps the fractionation of the major milk components by either sedimentation (Swaisgood, H. E., Developments in Dairy Chemistry-I: Chemistry of Milk Protein, (Applied Science Publishers, NY, 1982), precipitation (Kothe et al., U.S. Pat. No. 4644056); Groves, M. L. et al., (1985) Biochem. et. Biophys. Acta., 844:105–112; McKenzie, H. A., Milk Proteins: Chemistry and Molecular Biology, Academic Press, NY, 1971), 88) or enzymatic coagulation using rennin or chymotrypsin (Swaisgood, H. E., Developments in Dairy Chemistry-I: Chemistry of Milk Protein, (Applied Science Publishers, NY, 1982). Problems associated with these methods include low yields due to the loss of the protein of interest by entrapment in the precipitate of the milk component to be removed and loss of biological activity of the protein of interest due to the low pH often required for acid precipitation. See Denman, J. et al. (September 1991) Biotechnology 9: 839–843. Furthermore, because traditional methods of isolating proteins of interest from milk involved the sedimentation, precipitation, or coagulation of the major milk components, the milk samples were not readily processable by filtration.

SUMMARY OF THE INVENTION

The present invention pertains to a method of isolating a component of interest, such as a protein, from milk. The invention is based, at least in part, on the recognition that the low yields of biologically active components of interest obtained from milk samples using traditional methods were due essentially to entrapment of the component of interest in the precipitate of the initial fractionation step. The method of the present invention avoids inactivation and entrapment of the component of interest by providing a stabilizing agent which stabilizes the solubility of at least a portion of the total milk protein. Rather than being sedimented or precipitated out of the stabilized milk sample and carrying with it the component of interest, at least a portion of the total milk protein remains soluble such that it can be subsequently eliminated during purification of the component of interest. In addition, because the method of the present invention does not require the low pHs of the prior methods, inactivation of pH sensitive components of interest is avoided.

The present invention pertains to methods of isolating a component of interest in its biologically active form from a milk sample containing the component of interest. More particularly, the present invention relates to a method of isolating a component of interest from a milk sample by contacting the milk sample containing the component of interest with a stabilizing agent under conditions which stabilize the solubility of at least a portion of the total milk protein. After stabilization, the component of interest can be isolated without significant loss and the component of interest can be isolated from the stabilized milk sample in its biologically active form.

The present invention further pertains to a method of isolating a component of interest from a milk sample by contacting a milk sample containing a component of interest with a stabilizing agent forming a milk sample processable by filtration. The component of interest is then isolated from the milk sample processable by filtration.

The present invention even further pertains to components of interest isolated using the above-described methods and methods of stabilizing the solubility of at least a portion of the total milk protein in a milk sample containing a component of interest. The isolated components of interest can be used as additives to cell culture media, foodstuff preparations, and medicinal compositions. The invention even further pertains to kits containing reagents used in the above-described methods together with instructions for using the kit for stabilizing the solubility of at least a portion of the total milk protein of a milk sample containing a component of interest.

BRIEF DISCRIPTION OF THE DRAWINGS

DETAILED DESCRIPTION OF THE INVENTION

Figure 1:
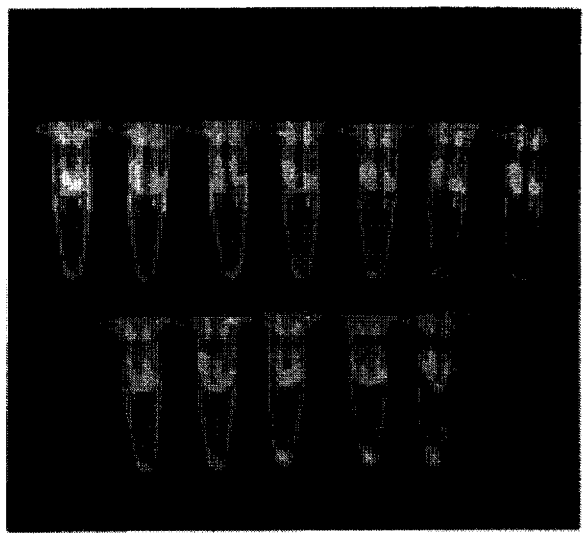
FIG. 1 is a photograph depicting the extent of solubilization of a portion of the total milk protein in milk samples over twelve different concentrations of arginine.

The present invention pertains to methods of isolating a component of interest from a milk sample containing the component of interest without significant loss of the component of interest. The method includes contacting a milk sample containing a component of interest with a stabilizing agent under conditions which stabilize the solubility of at least a portion of the total milk protein such that the component of interest can then be isolated from the stabilized milk sample. The component of interest is then isolated from the stabilized milk sample in a form which is biologically active.

The language "component of interest" is intended to include materials present in the milk sample capable of being isolated from the milk using the above-described method without significantly affecting the intended function of the component of interest in a detrimental manner. The component of interest can be a material naturally occurring in a milk sample or can be a material not normally present in a milk sample but which is targeted to the mammary tissue of a transgenic mammal and ultimately introduced into the milk of that mammal. The component of interest can be in free form or can be entrapped or encapsulated within another material present in the milk sample, e.g. a milk fat globule and/or the membrane encasing the milk fat globule (see, e.g. DiTullio et al. (1992) *Biotechnology* 10:74–77). Examples of components of interest include proteins, such as casein, lactoferrin, β-lactoglobulin, immunoglobulins, lipids, such as glycerides of oleic acid, palmitic acid, and myristic acid, polysaccharides, such as lactose and more complex oligosaccharides, or any of the above components in combination with vitamins, such as vitamins A and those of the B complex, and minerals, such as phosphorous, potassium, iron, magnesium, copper, and calcium For example, components of interest can be produced in the milk through normal secretory pathways. Normal secretory pathways for proteins can include synthesis of the protein in the rough endoplasmic reticulum, passage of the protein into the lumen of the endoplasmic reticulum followed by transportation to the Golgi apparatus. Finally, the proteins (or glycosylated proteins) are packaged into vesicles that are pinched off into the cytoplasm and subsequently fuse with the plasma membrane. Another secretion pathway involves the blebbing off of milk fat globules from the membrane which contain the component of interest, as in the case of cystic fibrosis transmembrane conductance regulator.

Naturally occurring milk components have been found to be useful as supplements for the serum-free growth of certain types of cells in culture. See Steimer, K. S. et al. (November 1981) *J. Cell Physiol.* 109(2):223–234 (epithelial cells and fibroblasts); Steimer, K. S. and Klagsbrun, M. (February 1981) *J. Cell Biol.* 88(2): 294–300 (normal and transformed fibroblasts). Milk components may also be used in foodstuffs. For example, the incorporation of milk components into bread can increase the nutritional value of the final product. e.g. Rudel, H. W. et al. (U.S. Pat. No. 5,178,894). Alternatively, milk components can be added to dairy products, such as frozen dairy desserts, to provide body and texture to the compositions and decrease the sensitivity of the product to temperature fluctuations. Huang, V. T. et al. (U.S. Pat. No. 5,175,013). Milk components can also be used to make cheeses. Yee, Jen-Jung et al. (U.S. Pat. No. 5,165,945).

The language "component of interest" is also intended to include any compound which is not normally present in a milk sample obtained from a nontransgenic mammal but is instead secreted in a milk sample obtained from a transgenic mammal. Examples of such components of interest include therapeutic agents. A therapeutic agent is an agent having a therapeutic effect on a mammal when administered at an appropriate dose under appropriate conditions. The desired therapeutic effect will depend on the disease or condition being treated. The afore-mentioned appropriate dose or conditions will be determined on an individual basis and will depend on such factors as the size of the individual being treated, the severity of the symptoms being treated, and the selected route for administration of the therapeutic agent. Examples of therapeutic agents include insulin, longer-acting tissue-type plasminogen activator (LA-tPA), antithrombin III, α-1-anti-trypsin, soluble CD4, interleukin-2, immunoglobulins, cystic fibrosis transmembrane conductance regulator, and coagulation factors VIII and IX.

The language "transgenic mammal" is intended to include a mammal whose cells, e.g. germline or somatic, have been genetically manipulated such that foreign DNA segments have been introduced therein. Examples of transgenic mammals include transgenic cows, sheep, goats, pigs, rabbits, rats, and mice. Typically, in order to obtain large scale production of the component of interest at a reduced cost, a mammal should be selected according to the amount of milk it produces. Preferably, large transgenic farm animals such as cows, sheep, and goats are chosen because of their ability to produce large volumes of milk.

The language "biologically active" is intended to include an activity for the component of interest which allows it to perform its intended function. The component of interest does not have to be as active as its naturally occurring counterpart but typically has an activity close to or similar to its naturally occurring counterpart.

The language "milk sample" is intended to include samples containing milk derived from a mammal which contain a component of interest. The milk sample can be a sample derived directly from the mammal or a sample which is processed in a manner which does not detrimentally affect the activity of the component of interest or the stabilizing agent's ability to perform is intended function. The milk sample further may be concentrated or diluted using reagents which do not detrimentally affect the activity of the component of interest or the stabilizing agent's ability to perform its intended function. The quantity of the milk present in the milk sample is an amount sufficient to ascertain the presence of the component of interest.

The language "stabilizing agent" is intended to include compounds which render soluble and/or maintain the solubility of at least a portion of the total milk protein and/or the component of interest. The language "maintain the solubility of" is intended to include the maintenance of the solubility to an extent that prevents the portion of the total milk protein from precipitating from the milk sample during later processing steps, e.g. pH adjustment, and interfering with the further processing of the milk sample or the isolation of the component of interest. This maintenance of solubility does not have to be the maintenance of the solubility at a constant value and can be the maintenance of the solubility over an appropriate range. Examples of such agents are mono- and polyvalent cationic agents such as amino acids and positively-charged buffers. Useful positively charged buffers include arginine, imidazole, and Bis-Tris. The pH of the stabilizing agent is typically selected such that the agent is positively-charged.

The language "stabilize the solubility" is intended to include solubilization and/or maintenance of the solubilization of at least a portion of the total milk protein. Certain of the major milk proteins, such as casein, are naturally in a partially insoluble or insoluble form in milk. Decreasing the pH of the milk can result in the precipitation of at least a portion of these milk proteins. However, the isolation of a component of interest may require that the pH of the milk sample be adjusted such that the component of interest becomes or remains soluble. Adjusting the pH of the milk sample may also tend to encourage precipitation of at least a portion of the total milk protein. The solubilizing agent solubilizes and/or maintains the solubility of these proteins before, during, and after a pH adjustment. Alternatively, isolation of other components of interest may not require the adjustment of the pH in order to become soluble or to maintain solubility but the solubilizing agent is still required to solubilize and/or maintain the solubility of at least a portion of the total milk protein allowing for the further processing of the milk sample without interference from precipitated milk proteins.

The concentration of the stabilizing agent is selected such that it preserves the functional properties of the component of interest and stabilizes the solubility of at least a portion of the total milk protein. For example, if the component of interest is an enzyme, the buffer concentration should be as low as possible since high ionic strength may decrease activity of the enzyme. The required concentration of the stabilizing agent in the isolation of a particular component of interest from milk will therefore vary according to the properties of the stabilizing agent itself and the component of interest to be isolated. For example, an arginine concentration of about 0.3M is more effective at preserving the functional properties of LA-tPA and stabilizing the solubility of at least a portion of the total milk protein than does 0.3M of imidazole.

The conditions under which the stabilizing agent is brought in contact with the milk sample to form a stabilized milk sample are selected such that the functional properties of the component of interest are preserved and the solubility of at least a portion of the total milk protein is stabilized. One of ordinary skill in the art would be able to manipulate, with only routine experimentation, conditions such as pH of the milk sample, the concentrations of the agents used for the isolation, and other factors that could affect the functional properties of the component of interest and the stability of the solubilization of at least a portion of the total milk protein.

The pH of the milk sample containing the component of interest should generally be adjusted to a level selected such that the component of interest retains its solubility and functional properties and the solubility of the portion of the total milk protein is stabilized. The level to which the pH is adjusted may be dictated by several factors. Included among these factors is the pH range within which the component of interest is in its natural and/or biologically active form. For example, certain components of interest, such as enzymes, may only be active within a narrow range of pHs and exposure to pHs outside this range can result in irreversible loss of activity. Therefore, in order to obtain the functional form of the component of interest or at least the component of interest in its natural form, the pH must be adjusted to levels only within the allowable range. A pH range from about 5.0 to about 9.0 is an example of a typical range within which many components of interest which have biological activity will retain that activity. The term "about 5.0" is defined below. The term "about 9.0" is intended to include pHs close to 9.0 which affect the component of interest in the same or similar manner as does pH 9.0, e.g. preferably 8.5 and above, more preferably 8.8 and above.

Another factor to consider in the adjustment of the pH is the level at which the solubility of at least a portion of the total milk protein is stabilized. The pH of the milk sample containing the protein of interest should generally not be lowered to the level or below the level at which milk components will precipitate from the milk. For example, the caseins precipitate at a pH of about 4.6 at 20° C. The pH should also be maintained at a level which prevents the component of interest from becoming insoluble. For example, the pH of the milk sample containing human longer-acting tissue-type plasminogen activator (LA-tPA) is generally lowered only to about 5.0 so that LA-tPA remains soluble. The term "about 5.0" is intended to include pHs close to 5.0 which affect the component of interest in the same or similar manner as does 5.0 e.g. preferably 4.6 to 5.4., more preferably 4.8 to 5.2.

The language "significant loss" is intended to include losses of the component of interest which would not allow the above-described method of isolating the component of interest to be a commercially feasible approach for producing the component of interest. The methods of this invention preferably have a loss of the component of interest which is less than 50%, more preferably less than about 20% and most preferably less than about 10%. The conventional methods for processing milk resulted in significant losses in yield of the component of interest because the component of interest was trapped in the sediment, precipitate, or coagulum. For example, Clark, A. J. et al., (May 1989) *Biotechnology* 7:487–492 reported a recovery of anti-hemophilic factor IX of about 2.0 to 2.5% using acid precipitation to remove milk caseins from a milk sample obtained from transgenic ewes. This translates into a loss of about 98%. Denman, J. et al., (September 1991) *Biotechnology* 9: 839–843 reported a recovery of LA-tPA of about 25%, and thus a loss of about 75%, using acid precipitation to remove milk caseins from a milk sample obtained from a transgenic dairy goat. Denman et al. also reported that other initial fractionation steps such as rennin treatment and acid pre-cipitation provided no significant increases in LA-tPA yields. Denman, J. et al. (September 1991) *Biotechnology* 9: 839–843.

The language "at least a portion of the total milk protein" is intended to include at least a portion of at least one protein which is normally present in milk in a partially insoluble or insoluble form. The portion of the total milk protein of which the solubility is stabilized must be in amount such that its removal constitutes more than an insignificant step in the isolation of a component of interest. The solubilities of portions of different milk proteins can be stabilized or the solubility of entire portions of one or more milk proteins can be stabilized. In the examples below, arginine and imidazole stabilized the solubility of at least a portion of the total milk protein in the examples described below, stabilized the solubility of at least the casein family of proteins, i.e. the entire portion or substantially the entire portion of at least one type of milk protein.

It should be understood that the component of interest can be isolated from the stabilized milk sample using conventional techniques. The selection of a separation or isolation technique is dependent on such factors as the type of component of interest being isolated and the amount of the component of interest present in the milk sample. Further, the isolation or separation of the component of interest from the stabilized milk sample can be performed using a single technique or a plurality of techniques in succession. These techniques include filtration and chromatographic techniques. Examples of filtration include dead-end filtration filter unit and cross-flow filtration. Examples of chromatographic techniques include ion exchange, hydrophobic, affinity, and gel-filtration chromatographic techniques. Similarly, further processing by fractionation of the milk sample prior to or after the isolation of the component of interest can be conducted using the above-described separation techniques. For example, fractionation of proteins and other components can be carried out by any of a variety of chromatographic methods depending on the properties of the component to be isolated. Proteins are most often fractionated by column chromatography, in which a mixture of proteins in solution is passed through a column containing a porous solid matrix, and they can be separately collected, in their native functional state, as they flow out of the bottom of the column. Depending on the type of matrix used, proteins are separated, for example, according to their charge (ion-exchange chromatography), their hydrophobicity (hydrophobic chromatography), their ability to bind to particular chemical groups (affinity chromatography) and their size (gel-filtration chromatography). For higher degrees of resolution, high performance liquid chromatography may be employed. Those skilled in the art will be able to vary the order and number of the above-described separation techniques with routine experimentation to isolate the component of the milk sample in which they are interested to the purity that they require.

The present invention further pertains to a method of isolating a component of interest from a milk sample by contacting a milk sample containing a component of interest with a stabilizing agent forming a milk sample processable by filtration. The component of interest may then be isolated from the milk sample processable by filtration. The terms component of interest and stabilizing agent are as defined above.

The language "processable by filtration" is intended to include a milk sample in which the solubility of at least a portion of the total milk protein is stabilized to an extent such that the stabilized milk sample is capable of passing through a filter and becoming part of the filtrate. The filters are of a type typically used to process milk or substances similar to milk. The filter generally contains pores of a size that typically would not be used for milk processing because the pores would become blocked by components in the milk. Examples of types of filters which can be used to process the milk samples of this invention include filters having pore sizes ranging from about 0.2 µm to about 5.0 µm. The component of interest can then be isolated from the filtrate by any of the methods for isolating proteins and in any order known to those of ordinary skill in the art. Some of these methods are described above.

The present invention further pertains to a method of stabilizing the solubility of at least a portion of the total milk protein in a milk sample containing the component of interest. The method involves contacting a milk sample with a stabilizing agent under conditions which stabilize the solubility of at least a portion of the total milk protein. The component of interest can be isolated from the stabilized milk sample without significant loss of the component of interest. The language "stabilizing agent", "under conditions which stabilize the solubility," and "at least a portion of the total milk protein" are as defined above.

The present invention also pertains to kits for stabilizing the solubility of at least a portion of the total milk protein of a milk sample containing a protein of interest. The kits include a container holding a stabilizing agent and instructions for using the stabilizing agent for the purpose of stabilizing the solubility of at least a portion of the total milk protein of a milk sample containing a component of interest to an extent which allows isolation of the component of interest from the stabilized milk sample without significant loss. The kits also may include a container for holding an agent for adjusting the pH of the milk sample to a level selected such that the biological activity of the component of interest is preserved and the solubility of the portion of the total milk protein is stabilized.

The language "agent for adjusting the pH" is intended to include compounds that are used by those of ordinary skill in the art to adjust the pH of a solution, such as a milk sample. Such agents include acids, such as HCl and acetic acid, and bases, such as NaOH. In addition, pH can also be regulated by gases, such as $CO_2$. In the case where the agent for adjusting the pH of the milk sample is in the form of a liquid, examples of containers which provide convenient means of delivering the pH adjusting agent include vials, bottles etc. that have caps which incorporate pipettes or medicine droppers.

The present invention is further illustrated by the following examples which should in no way be construed as being further limiting. The contents of all references and issued patents cited throughout all portions of this application (including the background) are expressly incorporated by reference. The present invention is further illustrated by the following examples.

EXAMPLE 1

Stabilization of the Solubility of Milk Protein from Milk of Transgenic Dairy Goats Containing Longer-Acting Tissue-Type Plasminogen Activator (LA-tPA) Using Arginine as the Stabilizing Agent Generation of transgenic goats The expression vector WAP-tPA was generated previously by fusing a 2–6 kb EcoRI-Kpnl fragment upstream of the murine whey acid protein gene to a cDNA encoding wild type human tPA. Gordon, K. et al (1987) *Bio/Technology* 5:1183–11875. This vector led to expression of tPA in milk of transgenic mice at levels as high as 250 µg/ml. A structural tPA variant was constructed (designated LAtPA) in which an asparagine to glutamine point mutation was introduced into the cDNA to produce a recombinant protein devoid of glycosylation at residue Asn 117. This longer acting tPA variant had an increased systemic half-life in a rabbit model. Lau, D. et al. (1987) *Bio/Technology* 5:953–958. A DNA fragment containing this point mutation in the tPA cDNA was substituted for this equivalent fragment in WAP-tPA to generate the vector used in this example, WAP-LAtPA.

Goats used as donor animals were of either Alpine or Saanen breeds. The timing of estrus was synchronized in the donors with norgestomet ear implants (Syncromate-B, CEVA Laboratories, Inc., Overland Park, Kans.; 6 mg). Prostaglandin was administered after the first 7–9 days to remove endogenous sources of progesterone. At day 13 following progesterone administration, follicle-stimulating hormone (FSH, Schering Corp., Kenilworth, N.J.) was given to goats at a dose of 18 mg over three days in twice daily injections. During the anestrus season, the dose of FSH was increased to 24 mg administered similarly over three days in twice daily injections. Twenty-four hours following implant removal, the donor animals were mated several times to fertile males over a two-day period. Recipient animals were synchronized by the same protocols as the donor animals except that a single non-superovulatory injection of pregnant mares serum gonadotropin (PMSG, Sigma, St. Louis, Mo.) was given on day 13 of progesterone treatment in place of the FSH. For five months, the recipients received 400 IU PMSG, and for the subsequent three months they received 750 IU PMSG. Recipient females were mated to vasectomized males to ensure estrus synchrony. Seventy-two hours following implant removal, embryos were recovered surgically from the oviducts of donors. Embryos were flushed from oviducts associated with ovulated ovaries through a cannula with sterile phosphate-buffered saline and were collected in a petri dish as previously reported. Selgrath, J. P. et al. (1990) *Theriogenology* 34:1195–1205. The HindIII-BamHI fragment of WAP-LAtPA was injected into one of the two pronuclei from one-cell embryos or into a nucleus of one blastomere of two-cell embryos at a concentration of 1 µg/ml. Embryos were surgically transferred into the oviducts of the recipient females or to the uteri following a 72 hour culture period. Pregnancies were confirmed by the inability of recipient mammals to return to natural estrus and by ultrasonic examination on days 45 and 55 of pregnancy.

Identification of transgenic goats

DNA was extracted from the buffy coat recovered from blood of goat #1. Following digestion with restriction enzymes, DNA was fractionated and blotted into nitrocellulose. Thomas, P. (1980) *Proc. Natl. Acad. Sci. U.S.A.* 77:5201–5205. The probe was 1.7 kb LAtPA cDNA isolated from the region of the whey acid protein gene 2600 bp upstream of the transcriptional start site. Gordon, K. et al (1987) *Bio/Technology* 5:1183–11875. The probe was radioactively labeled by the random primer method. Feinberg, A. et al (1983) *Anal. Biochem.* 72:248–254. At nine months of age, goat #1 was mated to a non-transgenic male. She became pregnant without difficulty and delivered two non-transgenic progeny. The transgenic mother was milked manually twice per day with an average daily yield of 3.4 liters. Ebert, K. M. et al. (1991) *Bio/Technology* 9: 835–838.

Milk samples obtained from lactating transgenic dairy goats generated according to the method of Ebert, K. M. et al. (September 1991) *Biotechnology* 9: 835–838 were stored frozen at −20° C. and thawed in a 37° C. water bath prior to analysis. The component of interest produced in the milk of the dairy goats was LA-tPA, a glycosylation variant of human tissue-type plasminogen activator which exhibits a longer circulating half-life than wild-type tPA.

Biochemical characterization of LAtPA

LAtPA has been expressed in the murine c127 cell line and purified and characterized for clinical testing. Cole, E. S. (1993) *Fibrinolysis* 7(1):15–22. LAtPA produced in this expression system was predominantly the single chain form of the protease, was partially glycosylated at position 184 and was variably sialylated, depending on the conditions of culture. Partial characterization of the purified transgenic LAtPA revealed a number of differences and similarities between it and the cell-derived protein. The transgenic enzyme, as isolated, existed in the "two chain" form, presumably due to proteolytic processing following its secretion into the milk. A similar observation was made with human tPA produced in the milk of transgenic mice. Gordon, K. et al. (1987) *Bio/Technology* 5:1183–1187; Pittius, C. W. et al. (1988) *Proc. Natl. Acad. Sci. U.S.A.* 85:5874–5878. Although the transgenic protein was glycosylated, there were significant differences in the oligosaccharide structures between transgenic and C127 cell-derived LAtPA. In particular, transgenic LAtPA contains N-acetylgalactosamine, which is absent in the C127 cell-derived enzyme. (See Denman, J. et al., cited supra, for a characterization of LA-tPA produced in the milk of transgenic dairy goats).

The pH of the milk sample was then adjusted from 6.7 to 5.0 using 1.0M acetic acid. The milk sample was subsequently divided into twelve 500 µl aliquots which were placed in 1.5 ml polypropylene tubes. A different amount of 2.0M arginine-HCl (pH 5.5) was added to each tube to obtain arginine concentrations ranging from 0.0M to 1.0M (Table I). Phosphate buffered saline (PBS) was added to bring the final volume up to 1.0 ml.

TABLE I

| ARGININE pH 5.5 | | | | |
|---|---|---|---|---|
| Final Arginine Concentration (M) | Milk (µl) | 2.0M Arginine (µl) | PBS (µl) | Final Volume (ml) |
| 1.00 | 500 | 500 | — | 1.0 |
| 0.90 | 500 | 450 | 50 | 1.0 |
| 0.80 | 500 | 400 | 100 | 1.0 |
| 0.70 | 500 | 350 | 150 | 1.0 |
| 0.60 | 500 | 300 | 200 | 1.0 |
| 0.50 | 500 | 250 | 250 | 1.0 |
| 0.40 | 500 | 200 | 300 | 1.0 |
| 0.30 | 500 | 150 | 350 | 1.0 |
| 0.20 | 500 | 100 | 400 | 1.0 |
| 0.10 | 500 | 50 | 450 | 1.0 |
| 0.05 | 500 | 25 | 475 | 1.0 |
| 0.00 | 500 | — | 500 | 1.0 |

The tubes were centrifuged for ten minutes at 1000 rpm in a Brinkman 5315 centrifuge. The tubes were removed and photographed to illustrate the extent of solubilization by examining the size of the casein pellet for each arginine concentration (FIG. 1). The supernatant was removed for quantitative analysis. FIG. 1 depicts the extent of solubilization of a portion of the total milk protein in milk samples over twelve different concentrations of arginine. For concentrations of arginine lower than 0.4M, protein (probably consisting mostly of casein) pellets were clearly visible. For concentrations of arginine greater than about 0.4M, there was little or no protein pellet.

The protein concentration of the supernatant was calculated by an absorbance measurement at 280 nm. The absorbance at 280 nm was taken by diluting each of the twelve supernatants 1:50 with PBS and reading on a Beckman DU-6 spectrophotometer. Each of the 12 samples had its own control blank diluted 1:50 with PBS wherein PBS was substituted for milk. LA-tPA activity was measured in an indirect amidolytic activity assay using the plasmin substrate Val-Leu-Lys-para-nitroanilide (S-2251, Helena Labs, Inc.) as described by Lau, D. et al. ((September 1987) *Biotechnology* 5: 953–958). Briefly, the plasmin substrate S-2251 was incubated with longer-acting tissue type plasminogen activator. The release of the chromophore p-nitroaniline after plasmin-mediated cleavage of the substrate was then measured by UV-visible spectroscopy at 405 nm and compared to suitable blanks which were previously generated.

Figure 2:
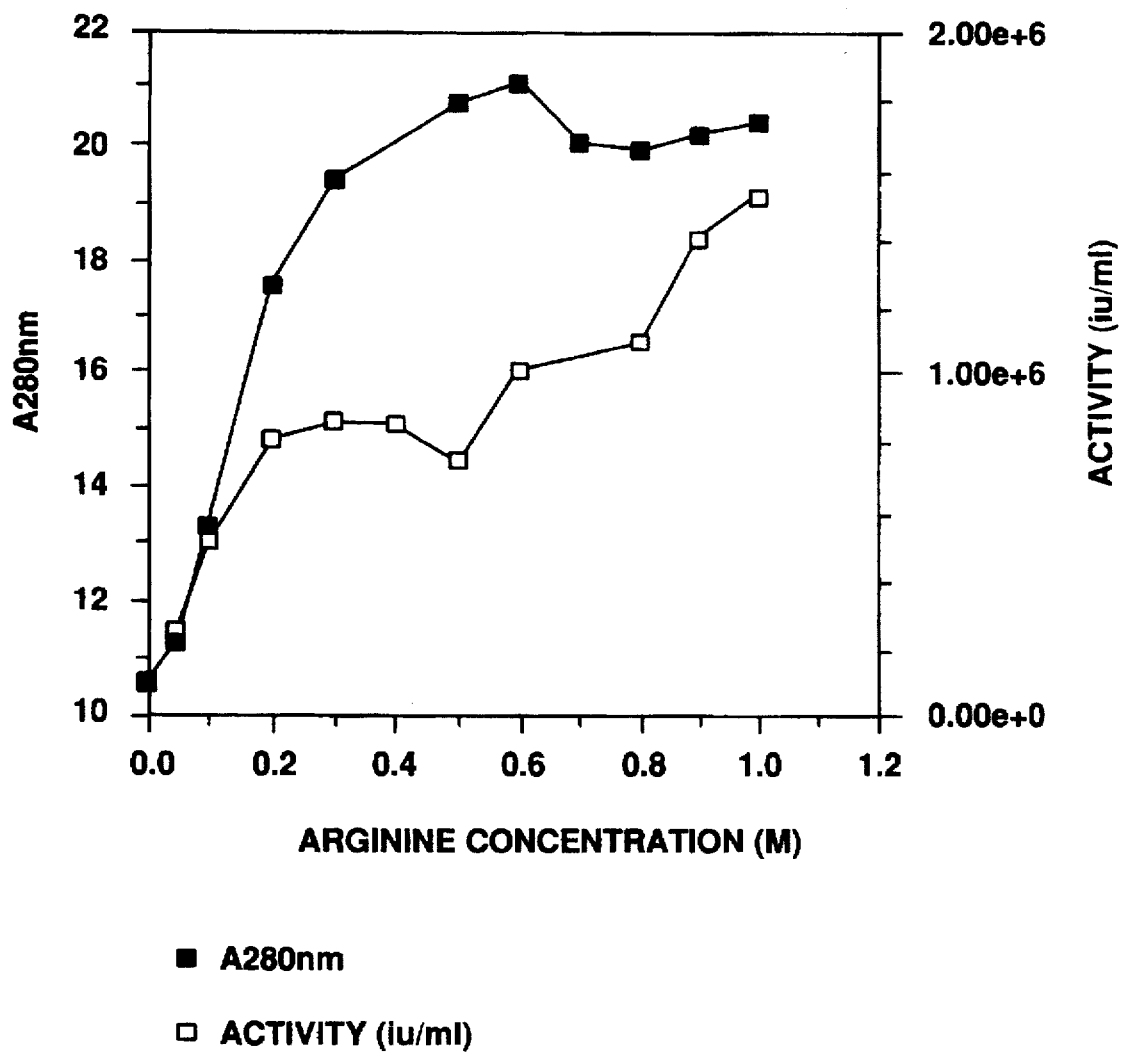
FIG. 2 depicts the relative protein concentration versus the longer-acting tissue-type plasminogen activator (LA-tPA) activity of the supernatant from the arginine solubilization step depicted in FIG. 1 for the twelve concentrations of arginine.

The results are set forth in FIG. 2. The dilution necessary was 1:500000. FIG. 2 depicts the relative protein concentration versus LA-tPA activity of supernatants over twelve concentrations of arginine (pH 5.5). The results in FIG. 2 demonstrate that as the amount of arginine increased, there was a concomitant rise in both the total protein concentration of the milk sample and the LA-tPA activity. These results demonstrate that arginine is able to stabilize the solubility of at least a portion of the total milk protein, thereby allowing isolation of increased amounts of LA-tPA.

EXAMPLE 2

Figure 3:
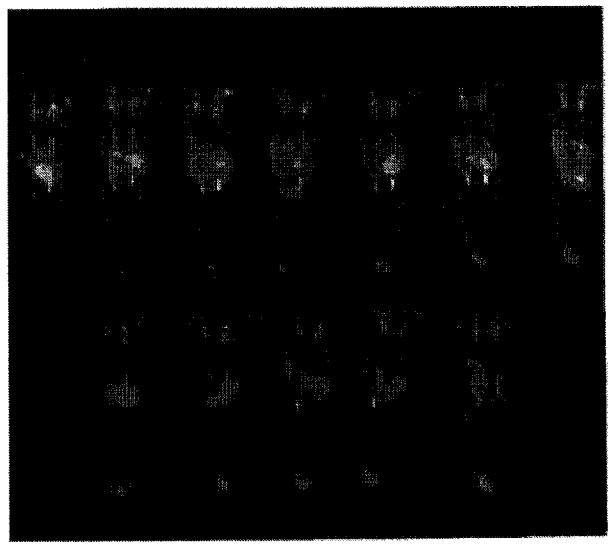
FIG. 3 is a photograph depicting the extent of solubilization of a portion of the total milk protein in milk samples over twelve different concentrations of imidazole.
Figure 4:
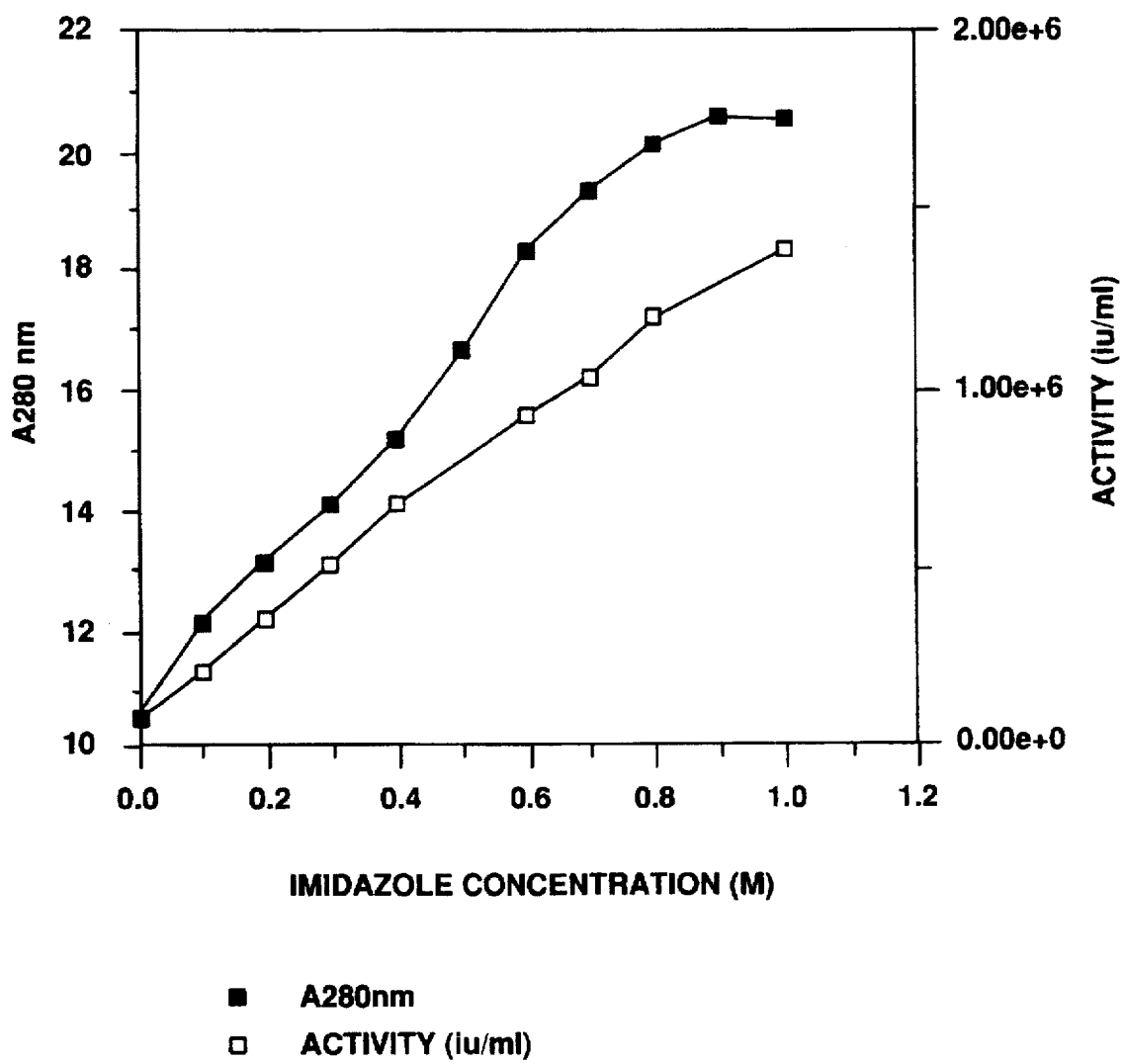
FIG. 4 depicts the relative protein concentration versus the LA-tPA activity of the supernatant from the imidazole solubilization step depicted in FIG. 3 for the twelve concentrations of imidazole.

Stabilization of the Solubility of Milk Protein from Milk of Transgenic Dairy Goats Containing LA-tPA Using Imidazole as the Stabilizing Agent The procedure described in Example 1 was followed except that 2.0M imidazole (pH 7.0) was substituted for arginine. Table II sets forth the range of concentrations of imidazole tested. FIG. 3 is a photograph illustrating the extent of solubilization of the milk sample over the range of imidazole concentrations. For concentrations of imidazole lower than about 0.7M, protein (probably consisting mostly of casein) pellets were clearly visible. For concentrations of arginine greater than about 0.7M, there was little or no protein pellet. FIG. 4 depicts the relative protein concentration of the supernatant versus the LA-tPA activity over the twelve concentrations of imidazole. As, in the case of arginine, imidazole was able to stabilize the solubility of at least a portion of the total milk protein, thereby allowing an increased yields of LA-tPA. FIG. 4 shows that there was a concomitant increase in the total protein concentration of the milk sample and the LA-tPA activity as the concentration of imidazole in the milk sample increased.

TABLE II

IMIDAZOLE pH 7.0

| Final Imidazole Concentration (M) | Milk (µl) | 2.0M Imidazole (µl) | PBS (µl) | Final Volume (ml) |
|---|---|---|---|---|
| 1.00 | 500 | 500 | — | 1.0 |
| 0.90 | 500 | 450 | 50 | 1.0 |
| 0.80 | 500 | 400 | 100 | 1.0 |
| 0.70 | 500 | 350 | 150 | 1.0 |
| 0.60 | 500 | 300 | 200 | 1.0 |
| 0.50 | 500 | 250 | 250 | 1.0 |
| 0.40 | 500 | 200 | 300 | 1.0 |
| 0.30 | 500 | 150 | 350 | 1.0 |
| 0.20 | 500 | 100 | 400 | 1.0 |
| 0.10 | 500 | 50 | 450 | 1.0 |
| 0.05 | 500 | 25 | 475 | 1.0 |
| 0.00 | 500 | — | 500 | 1.0 |

EXAMPLE 3

Stabilization of the Solubility of Milk Protein from Milk of Transgenic Dairy Goats Containing LA-tPA Using Bis-Tris as the Stabilizing Agent The procedure described in Example 1 was followed except that 1.7M Bis-Tris (pH 6.0) was substituted for arginine and the range of concentrations of Bis-Tris tested was narrower than the range of concentrations of arginine tested. Table III sets forth the range of concentrations of Bis-Tris used in the experiment.

TABLE III

BIS-TRIS pH 6.0

| Final Bis-Tris Concentration (M) | Milk (µl) | 1.7M Bis-Tris (µl) | PBS (µl) | Final Volume (ml) |
|---|---|---|---|---|
| 0.85 | 500 | 500 | — | 1.0 |
| 0.80 | 500 | 471 | 29 | 1.0 |
| 0.70 | 500 | 412 | 88 | 1.0 |
| 0.60 | 500 | 353 | 347 | 1.0 |
| 0.50 | 500 | 294 | 206 | 1.0 |
| 0.40 | 500 | 235 | 265 | 1.0 |
| 0.30 | 500 | 176 | 324 | 1.0 |
| 0.20 | 500 | 118 | 382 | 1.0 |
| 0.10 | 500 | 59 | 441 | 1.0 |
| 0.00 | 500 | — | 500 | 1.0 |

Figure 5:
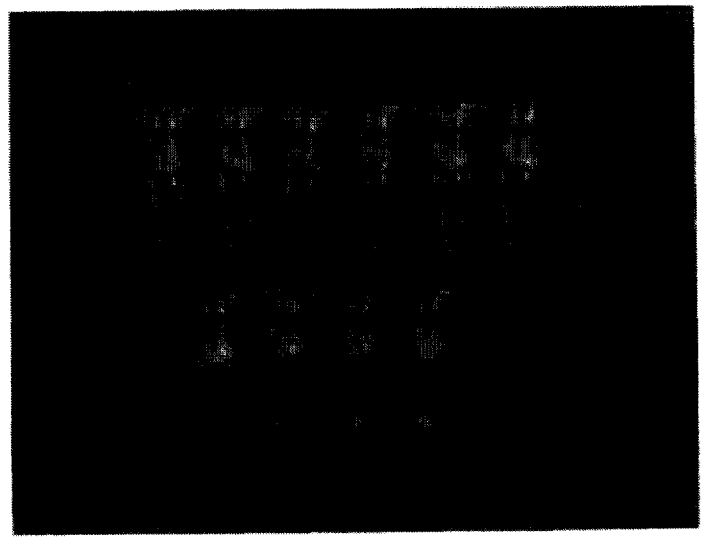
FIG. 5 is a photograph depicting the extent of solubilization of a portion of the total milk protein in milk samples over ten different concentrations of Bis-Tris.
Figure 6:
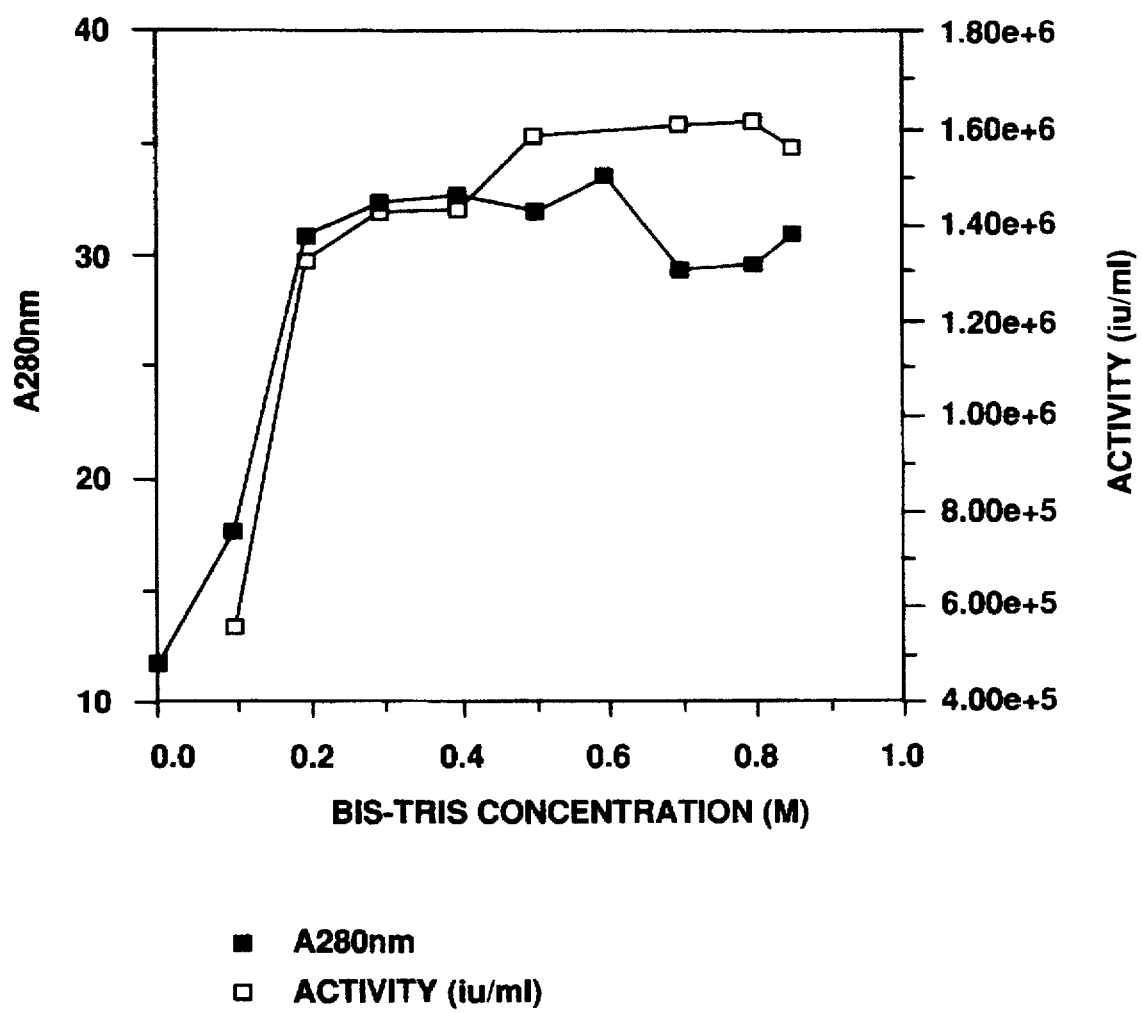
FIG. 6 depicts the relative protein concentration versus the LA-tPA activity of the supernatant from the Bis-Tris solubilization step depicted in FIG. 5 for the ten concentrations of Bis-Tris.
Figure 7A:
FIGS. 7A–7E are five photographs depicting the extent of solubilization of a portion of the total milk protein in milk samples for various concentrations of arginine over a range of pHs.
Figure 7B:
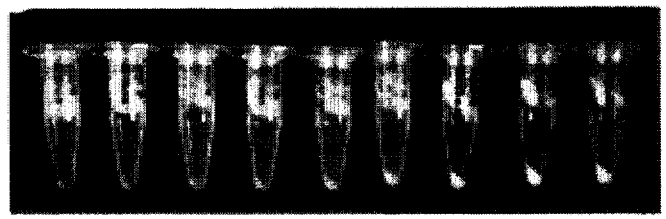
Figure 7C:
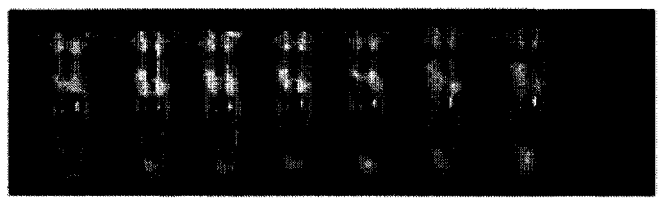
Figure 7D:
Figure 7E:
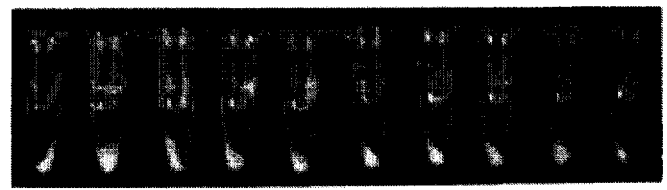

FIG. 5 is a photograph illustrating the extent of solubilization of the milk sample over the range of Bis-Tris concentrations tested by depicting the size of the protein pellet. For concentrations of Bis-Tris as low as 0.2M, there was little to no protein pellet visible. FIG. 6 depicts the relative protein concentration of the supernatant versus the LA-tPA activity over the ten concentrations of Bis-Tris. FIG. 6 shows that there was a concomitant increase in the total protein concentration of the milk sample and the LA-tPA activity as the concentration of Bis-Tris in the milk sample increased with a decrease in LA-tPA activity at Bis-Tris concentrations of about 0.65M and greater.

EXAMPLE 4

Stabilization of the Solubility of Milk Protein from Milk of Transgenic Dairy Goats Containing LA-tPA Using Arginine at Different pHs as the Solubilizing Agent The initial pH of the milk sample was 6.7. From this point the pH of the sample was adjusted to the desired pH, e.g. 4.3, 6.0, 7.0, and 8.0. The pH of the milk sample was not adjusted in the case where the pH of the stabilizing agent to be tested was 6.7. The 2.0M arginine was similarly adjusted to the pH of the sample to which it was to be added to prevent fluctuations in the pH of the final sample. The pH-adjusted milk samples were then divided into 500 µl aliquots which were placed in 1.5 ml polypropylene tubes. Varying amounts of 2.0M arginine were added to the milk samples to obtain milk samples containing arginine at various concentrations and at various pHs. PBS was added to bring the final volume up to 1.0 ml.

The tubes were centrifuged for 10 minutes at 1000 rpm in a Brinkman 5315 centrifuge. The tubes were then removed and photographed to illustrate the extent of solubilization by examining the size of the protein pellet for each arginine concentration at pHs 4.3, 6.0, 6.7, 7.0, and 8.0. These photographs are depicted in FIG. 7A–E. As shown in FIG. 7A–E, the arginine at pH 6.0 acted as the best stabilizer of the solubility of the milk protein over a range arginine concentrations from about 0.5M to about 1.0M. Arginine at pH 7.0 at concentrations ranging from about 0.6M to 1.0M was also a good stabilizer of the solubility of the milk protein. Arginine at pH 4.3 demonstrated poor stabilization of the milk protein over a range of concentrations from about 0.1M to about 1.0M.

EXAMPLE 5

Figure 8:
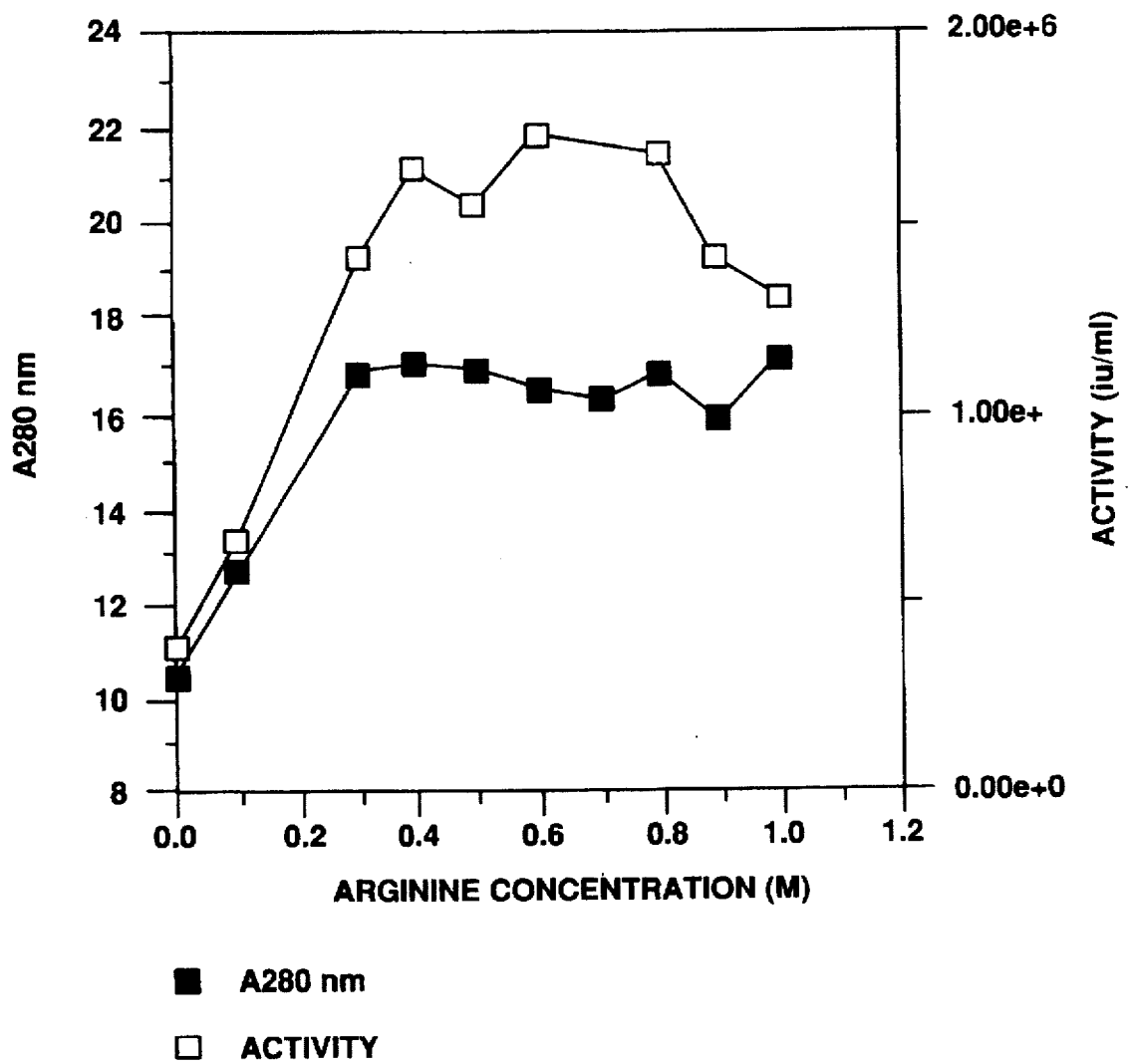
FIG. 8 depicts the relative protein concentration versus the LA-tPA activity of the supernatant from an arginine-mediated solubilization of a portion of the total milk protein wherein the arginine was added to the milk sample prior to adjustment of the pH of the milk sample.

Isolation of LA-tPA from the Milk of Transgenic Dairy Goats By First Adding Arginine and then Adjusting the pH of the Milk Sample The procedure described in Example 1 was followed except that 2.0M arginine (pH 5.5) was added prior to the pH adjustment. The range of concentrations of arginine tested in the experiment was the same as that tested in Example 1 and is set forth in Table I. FIG. 8 depicts the relative protein concentration of the supernatant versus the LA-tPA activity over the twelve concentrations of arginine. A rise in both the total milk protein concentration and the LA-tPA activity accompanied the increase in arginine concentration. LA-tPA activity, however, peaked for an arginine concentration of about 1.0M at a level (about 1.20e+6 IU/ml) as compared to the peak LA-tPA activity (about 1.50e+6IU/ml) in Example 1 for the same arginine concentration.

EXAMPLE 6

Isolation of Anti-Thrombin III from the Milk of a Transgenic Mouse Using Arginine as the Stabilizing Agent Milk samples obtained from a lactating transgenic mouse were stored frozen at −80° C. and thawed at room temperature prior to analysis. The component of interest produced in the milk of the mouse was human anti-thrombin III.

The pH of the milk sample was not adjusted because the volume was too small. The milk sample was subsequently divided into two 500 µl aliquots which were placed in 1.5 ml polypropylene tubes. A 500 µl aliquot of 2.0M arginine, pH 5.0, was added to one tube and 100 µl of 1.0M epsilon-amino caproic acid (EACA) was added to the other tube with 400 µl of PBS to equalize the volumes at 1.0 ml in each tube. The tube contents were filtered using a 0.45 µm filter unit (Millipore, Bedford, Mass.). Results showed that the arginine containing sample was easy to filter and the recovery was 83% of the starting anti-thrombin III. The material with the EACA was extremely difficult to filter and the recovery of anti-thrombin III was 50%.

EXAMPLE 7

Isolation of LA-tPA from the Milk of Transgenic Dairy Goats Using Arginine as the Solubilizing Agent The milk was thawed at room temperature, adjusted to pH 5.0 using 1.0M acetic acid, diluted with an equal volume of 1.0M arginine and dead-end filtered through a 0.22 µm nominal filter (Sartorius, Bohemia, N.Y.) followed by a 0.20 µm absolute filter (Millipore, Bedford, Mass.). LA-tPA was purified from the filtrate by initially binding the enzyme to a TSK-butyl column. The column was equilibrated and washed in 20 mM sodium phosphate (pH 6.0), 100 mM arginine-HCl, 0.01%. TWEEN 80 TM, a monsoliate biological detergent and step eluted using 20 mM sodium phosphate, 100 mM arginine-HCl and 70% ethylene glycol. Elution pool collection was accomplished by monitoring by absorbance at 280 nm at 1.0 AUFS. Collection started at the first deflection above baseline. This initial step provides a means of concentrating and substantially purifying the enzyme. Recovery of LA-tPA from this procedure was 95% of the starting activity compared with 25 to 50% recoveries observed without the addition of arginine.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of isolating a protein of intrest from a milk sample, comprising:
   contacting a milk sample containing a protein of interest with a cationic solubilizing agent under conditions which stabilize the solubility of at least a portion of the total milk protein such that the protein of interest can be isolated from the solubilized milk sample with less than 50% loss of the protein of interest; and
   isolating the protein of interest from the solubilized milk sample in a form which is biologically active.

2. The method of claim 1 wherein the milk sample is obtained from a transgenic mammal.

3. The method of claim 1 wherein the protein of interest is a naturally occurring milk protein.

4. The method of claim 1 wherein the protein of interest is a protein secreted in the milk of a transgenic mammal.

5. The method of claim 1 wherein the protein of interest is a therapeutic agent.

6. The method of claim 5 wherein the therapeutic agent is longer-acting tissue-type plasminogen activator.

7. The method of claim 5 wherein the therapeutic agent is anti-thrombin III.

8. The method of claim 1 wherein the protein of interest is an immunoglobulin.

9. The method of claim 1 wherein the pH of the milk sample containing the cationic solubilizing agent ranges from about 5.0 to about 9.0.

10. The method of claim 1 wherein the catonic solubilizing agent is arginine.

11. The method of claim 1 wherein the cationic solubilizing agent is imidazole.

12. The method of claim 1 wherein the cantonic solubilizing agent is Bis-Tris.

13. The method of claim 1 further comprising filtering of the milk sample and isolating the protein of interest from the filtrate.

14. The method of claim 1 wherein the protein of intrest is isolated from the filtrate by chromatography.

15. The method of claim 1 wherein the loss of the protein of interest is less than about 20%.

16. The method of claim 1 wherein the loss of the protein of interest is less than about 10%.

* * * * *